(12) United States Patent
Yue et al.

(10) Patent No.: US 9,896,734 B2
(45) Date of Patent: Feb. 20, 2018

(54) ASPARAGINIC ACID KINASE III MUTANT AND HOST CELLS AND USE THEREOF

(71) Applicants: COFCO BIOCHEMICAL (ANHUI) CO., LTD, Bengbu, Anhui (CN); TIANJIN INSTITUTE OF INDUSTRIAL BIOTECHNOLOGY, CHINESE ACADEMY OF SCIENCES, Tianjin (CN)

(72) Inventors: Guojun Yue, Anhui (CN); Jibin Sun, Tianjin (CN); Ping Zheng, Tianjin (CN); Jiao Liu, Tianjin (CN); Qinggang Li, Tianjin (CN); Linghe Xia, Anhui (CN); Yongsheng Zhou, Anhui (CN); Hu Luo, Anhui (CN); Yong Zhou, Anhui (CN); Yun Man, Anhui (CN); Zongmei Lu, Anhui (CN); Yanhe Ma, Tianjin (CN)

(73) Assignees: Cofco Biochemical (Anhui) Co., Ltd., Anhui (CN); Tianjin Institute of Industrial Biotechnology, Chinese Academy of Sciences, Tianjin (CN)

( * ) Notice: Subject to any disclaimer, the term of this patent is extended or adjusted under 35 U.S.C. 154(b) by 0 days.

(21) Appl. No.: 14/437,115

(22) PCT Filed: May 16, 2013

(86) PCT No.: PCT/CN2013/075751
§ 371 (c)(1),
(2) Date: Apr. 20, 2015

(87) PCT Pub. No.: WO2014/059789
PCT Pub. Date: Apr. 24, 2014

(65) Prior Publication Data
US 2015/0337346 A1 Nov. 26, 2015

(30) Foreign Application Priority Data
Oct. 18, 2012 (CN) .......................... 2012 1 0398902

(51) Int. Cl.
*C12P 13/08* (2006.01)
*C12P 13/06* (2006.01)
*C12P 13/12* (2006.01)
*C12N 9/12* (2006.01)

(52) U.S. Cl.
CPC .... *C12Y 207/02004* (2013.01); *C12N 9/1217* (2013.01); *C12P 13/06* (2013.01); *C12P 13/08* (2013.01); *C12P 13/12* (2013.01)

(58) Field of Classification Search
CPC .. C12N 9/12; C12P 13/12; C12P 13/06; C12P 13/08
See application file for complete search history.

(56) References Cited

U.S. PATENT DOCUMENTS

| | | | |
|---|---|---|---|
| 5,661,012 A | 8/1997 | Sano et al. | |
| 9,090,882 B2 * | 7/2015 | Crowley | C12N 9/1217 |
| 2010/0173368 A1 | 7/2010 | Nakanishi et al. | |
| 2010/0190216 A1 | 7/2010 | Gunji et al. | |
| 2011/0191898 A1 * | 8/2011 | Crowley | C12N 9/1217 |
| | | | 800/278 |

FOREIGN PATENT DOCUMENTS

| | | |
|---|---|---|
| CN | 1107179 | 8/1995 |
| CN | 1182133 | 5/1998 |
| CN | 1203629 | 12/1998 |
| CN | 1071378 | 9/2001 |
| EP | 1394257 | 3/2004 |
| WO | 2012/056318 | 5/2012 |
| WO | WO 2012/056318 * | 5/2012 |

OTHER PUBLICATIONS

Aspartokinase [Rickettsia bellii RML369-C] (created on Apr. 5, 2006).*
Ogata et al. Genome sequence of Rickettsia bellii illuminates the role of amoebae in gene exchanges between intracellular pathogens. PLoS Genet. (2006), vol. 2(5):e76, pp. 733-744.*
Yoshida et al., Mechanism of Concerted Inhibition of α2β2-type Hetero-oligomeric Aspartate Kinase from Corynebacterium glutamicum., The Journal of Biological Chemistry (2006), vol. 285, pp. 27477-27486.*
C. glutamicum Aspartokinase (last viewed on Jan. 31, 2017).*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*

(Continued)

*Primary Examiner* — David Steadman
(74) *Attorney, Agent, or Firm* — Hamre, Schumann, Mueller & Larson, P.C.

(57) ABSTRACT

Provided in the present invention is an asparaginic acid kinase, and the 340$^{th}$ amino acid residue in the position of the amino acid sequence of the asparaginic acid kinase corresponding to the amino acid sequence shown in SEQ ID NO: 2 is a non-aspartic acid. The asparaginic acid of the present invention can efficiently relieve the feedback inhibition of L-lysine, and can be effectively used for the production of L-lysine. Also provided in the present invention are host cells comprising genes coding the asparaginic acid kinase and a method for producing L-lysine using the host cells or the asparaginic acid kinase. The asparaginic acid kinase of the present invention or the host cells comprising the asparaginic acid kinase of the present invention is also used to produce L-threonine, L-methionine, L-isoleucine or L-valine. Also provided in the present invention is a method of producing L-aspartyl-4-yl phosphoric acid using the asparaginic acid kinase or the host cells.

14 Claims, 1 Drawing Sheet

(56) References Cited

OTHER PUBLICATIONS

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Branden and Tooze, Introduction to Protein Structure (1999), 2nd edition, Garland Science Publisher, pp. 3-12.*

International Search Report for application No. PCT/CN2013/075751, dated Aug. 22, 2013 (10 pages).

X. Dong et al., "Metabolic engineering of *Escherichia coli* and *Corynebacterium glutamicum* for the production of L-threonine," Biotechnology Advances, vol. 29 (2011), p. 11-23.

E. R. Stadtman et al., "Feed-back Inhibition and Repression of Aspartokinase Activity in *Escherichia coli* and *Saccharomyces cerevisiae*," The Journal of Biological Chemistry, vol. 236, No. 7 (Jul. 1961), p. 2033-2038.

* cited by examiner

SEQUENCE LISTING

<160> NUMBER OF SEQ ID NOS: 27

<210> SEQ ID NO 1
<211> LENGTH: 1350
<212> TYPE: DNA
<213> ORGANISM: Escherichia coli

<400> SEQUENCE: 1

```
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag gactggaacc tggcgagcga     180
ttcgaaaaac tcgacgctat ccgcaacatc cagtttgcca ttctggaacg tctgcgttac     240
ccgaacgtta tccgtgaaga gattgaacgt ctgctggaga acattactgt tctggcagaa     300
gcggcggcgc tggcaacgtc tccggcgctg acagatgagc tggtcagcca cggcgagctg     360
atgtcgaccc tgctgtttgt tgagatcctg cgcgaacgcg atgttcaggc acagtggttt     420
gatgtacgta aagtgatgcg taccaacgac cgatttggtc gtgcagagcc agatatagcc     480
gcgctggcgg aactggccgc gctgcagctg ctcccacgtc tcaatgaagg cttagtgatc     540
acccagggat ttatcggtag cgaaaataaa ggtcgtacaa cgacgcttgg ccgtggaggc     600
agcgattata cggcagcctt gctggcggag gctttacacg catctcgtgt tgatatctgg     660
accgacgtcc cgggcatcta caccaccgat ccacgcgtag tttccgcagc aaaacgcatt     720
gatgaaatcg cgtttgccga agcggcagag atggcaactt ttggtgcaaa agtactgcat     780
ccggcaacgt tgctacccgc agtacgcagc gatatcccgg tctttgtcgg ctccagcaaa     840
gacccacgcg caggtgtac gctggtgtgc aataaaactg aaaatccgcc gctgttccgc     900
gctctggcgc ttcgtcgcaa tcagactctg ctcactttgc acagcctgaa tatgctgcat     960
tctcgcggtt tcctcgcgga agtttcggc atcctcgcgc ggcataatat ttcggtagac    1020
ttaatcacca cgtcagaagt gagcgtggca ttaaccttg ataccaccgg ttcaacctcc    1080
```

-continued

```
actggcgata cgttgctgac gcaatctctg ctgatggagc tttccgcact gtgtcgggtg    1140
gaggtggaag aaggtctggc gctggtcgcg ttgattggca atgacctgtc aaaagcctgc    1200
ggcgttggca agaggtatt cggcgtactg gaaccgttca acattcgcat gatttgttat    1260
ggcgcatcca gccataacct gtgcttcctg gtgcccggcg aagatgccga gcaggtggtg    1320
caaaaactgc atagtaattt gtttgagtaa                                     1350
```

<210> SEQ ID NO 2
<211> LENGTH: 449
<212> TYPE: PRT
<213> ORGANISM: Escherichia coli

<400> SEQUENCE: 2

```
Met Ser Glu Ile Val Val Ser Lys Phe Gly Gly Thr Ser Val Ala Asp
1               5                  10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Ile Glu Arg Leu Leu Glu Asn Ile Thr
                85                  90                  95

Val Leu Ala Glu Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320
```

```
Ser Arg Gly Phe Leu Ala Glu Val Phe Gly Ile Leu Ala Arg His Asn
            325                 330                 335

Ile Ser Val Asp Leu Ile Thr Thr Ser Glu Val Ser Val Ala Leu Thr
        340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
        370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
            405                 410                 415

Met Ile Cys Tyr Gly Ala Ser Ser His Asn Leu Cys Phe Leu Val Pro
        420                 425                 430

Gly Glu Asp Ala Glu Gln Val Val Gln Lys Leu His Ser Asn Leu Phe
            435                 440                 445

Glu
```

<210> SEQ ID NO 3
<211> LENGTH: 1350
<212> TYPE: DNA
<213> ORGANISM: Artificial sequence
<220> FEATURE:
<223> OTHER INFORMATION: oligonucleotide

<400> SEQUENCE: 3

| | | | | | |
|---|---|---|---|---|---|
| atgtctgaaa | ttgttgtctc | caaatttggc | ggtaccagcg | tagctgattt | tgacgccatg | 60 |
| aaccgcagcg | ctgatattgt | gctttctgat | gccaacgtgc | gtttagttgt | cctctcggct | 120 |
| tctgctggta | tcactaatct | gctggtcgct | ttagctgaag | gactggaacc | tggcgagcga | 180 |
| ttcgaaaaac | tcgacgctat | ccgcaacatc | cagtttgcca | ttctggaacg | tctgcgttac | 240 |
| ccgaacgtta | tccgtgaaga | gattgaacgt | ctgctggaga | acattactgt | tctggcagaa | 300 |
| gcggcggcgc | tggcaacgtc | tccggcgctg | acagatgagc | tggtcagcca | cggcgagctg | 360 |
| atgtcgaccc | tgctgttttgt | tgagatcctg | cgcgaacgcg | atgttcaggc | acagtggttt | 420 |
| gatgtacgta | aagtgatgcg | taccaacgac | cgatttggtc | gtgcagagcc | agatatagcc | 480 |
| gcgctggcgg | aactggccgc | gctgcagctg | ctcccacgtc | tcaatgaagg | cttagtgatc | 540 |
| acccagggat | ttatcggtag | cgaaaataaa | ggtcgtacaa | cgacgcttgg | ccgtggaggc | 600 |
| agcgattata | cggcagcctt | gctggcggag | gctttacacg | catctcgtgt | tgatatctgg | 660 |
| accgacgtcc | cgggcatcta | caccaccgat | ccacgcgtag | tttccgcagc | aaaacgcatt | 720 |
| gatgaaatcg | cgtttgccga | agcggcagag | atggcaactt | tggtgcaaaa | gtactgcat | 780 |
| ccggcaacgt | tgctacccgc | agtacgcagc | gatatcccgg | tctttgtcgg | ctccagcaaa | 840 |
| gacccacgcg | caggtggtac | gctggtgtgc | aataaaactg | aaaatccgcc | gctgttccgc | 900 |
| gctctggcgc | ttcgtcgcaa | tcagactctg | ctcactttgc | acagcctgaa | tatgctgcat | 960 |
| tctcgcggtt | cctcgcggga | agttttcggc | atcctcgcgc | ggcataatat | tcggtaccg | 1020 |
| ttaatcacca | cgtcagaagt | gagcgtggca | ttaacccttg | ataccaccgg | ttcaacctcc | 1080 |
| actggcgata | cgttgctgac | gcaatctctg | ctgatggagc | tttccgcact | gtgtcgggtg | 1140 |
| gaggtggaag | aaggtctggc | gctggtcgcg | ttgattggca | atgacctgtc | aaaagcctgc | 1200 |
| ggcgttggca | aagaggtatt | cggcgtactg | gaaccgttca | acattcgcat | gatttgttat | 1260 |
| ggcgcatcca | gccataacct | gtgcttcctg | gtgcccggcg | aagatgccga | gcaggtggtg | 1320 | caaaaactgc atagtaattt gtttgagtaa 1350

<210> SEQ ID NO 4
<211> LENGTH: 449
<212> TYPE: PRT
<213> ORGANISM: Artificial sequence
<220> FEATURE:
<223> OTHER INFORMATION: polypeptide

<400> SEQUENCE: 4

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Pro Leu Ile Thr Thr Ser Glu Val Ser Val Ala Leu Thr
            340                 345                 350
```

```
Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 5
<211> LENGTH: 1350
<212> TYPE: DNA
<213> ORGANISM: Artificial sequence
<220> FEATURE:
<223> OTHER INFORMATION: polynucleotide

<400> SEQUENCE: 5
atgtctgaaa ttgttgtctc caaatttggc ggtaccagcg tagctgattt tgacgccatg      60
aaccgcagcg ctgatattgt gcttttctgat gccaacgtgc gtttagttgt cctctcgggct    120
tctgctggta tcactaatct gctggtcgct ttagctgaag gactggaacc tggcgagcga     180
ttcgaaaaac tcgacgctat ccgcaacatc cagtttgcca ttctggaacg tctgcgttac     240
ccgaacgtta ccgtgaaga gattgaacgt ctgctggaga acattactgt tctggcagaa     300
gcggcggcgc tggcaacgtc tccggcgctg acagatgagc tggtcagcca cggcgagctg    360
atgtcgaccc tgctgtttgt tgagatcctg cgcgaacgcg atgttcaggc acagtggttt    420
gatgtacgta aagtgatgcg taccaacgac cgatttggtc gtgcagagcc agatatagcc    480
gcgctggcgg aactggccgc gctgcagctg ctcccacgtc tcaatgaagg cttagtgatc    540
acccagggat ttatcggtag cgaaaataaa ggtcgtacaa cgacgcttgg ccgtggaggc    600
agcgattata cggcagcctt gctggcggag gctttacacg catctcgtgt tgatatctgg    660
accgacgtcc cggcatctta ccaccaccgat ccacgcgtag tttccgcagc aaaacgcatt    720
gatgaaatcg cgtttgccga agcggcagag atggcaactt ttggtgcaaa agtactgcat    780
ccggcaacgt tgctacccgc agtacgcagc gatatcccgg tctttgtcgg ctccagcaaa    840
gacccacgcg caggtggtac gctggtgtgc aataaaactg aaaatccgcc gctgttccgc    900
gctctggcgc ttcgtcgcaa tcagactctg ctcactttgc acagcctgaa atgctgcat    960
tctcgcggtt tcctcgcgga agttttcggc atcctcgcgc ggcataatat tcggtagtc   1020
ttaatcacca cgtcagaagt gagcgtggca ttaaccttg ataccaccgg ttcaacctcc   1080
actggcgata cgttgctgac gcaatctctg ctgatggagc tttccgcact gtgtcgggtg   1140
gaggtggaag aagtctggc gctggtcgcg ttgattggca atgacctgtc aaaagcctgc   1200
ggcgttggca agaggtatt cggcgtactg gaaccgttca acattcgcat gatttgttat   1260
ggcgcatcca gccataacct gtgcttcctg gtgcccggcg aagatgccga gcaggtggtg   1320
caaaaactgc atagtaattt gtttgagtaa                                   1350

<210> SEQ ID NO 6
<211> LENGTH: 449
```

```
<212> TYPE: PRT
<213> ORGANISM: Artificial sequence
<220> FEATURE:
<223> OTHER INFORMATION: polypeptide

<400> SEQUENCE: 6
```

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Val Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
            405                 410                 415

Met Ile Cys Tyr Gly Ala Ser Ser His Asn Leu Cys Phe Leu Val Pro
        420                 425                 430

Gly Glu Asp Ala Glu Gln Val Val Gln Lys Leu His Ser Asn Leu Phe
    435                 440                 445

Glu

<210> SEQ ID NO 7
<211> LENGTH: 1350
<212> TYPE: DNA
<213> ORGANISM: Artificial sequence
<220> FEATURE:
<223> OTHER INFORMATION: polynucleotide

<400> SEQUENCE: 7
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag actggaacc tggcgagcga     180 ttcgaaaaac tcgacgctat ccgcaacatc cagtttgcca ttctggaacg tctgcgttac     240
ccgaacgtta tccgtgaaga gattgaacgt ctgctggaga acattactgt tctggcagaa     300
gcggcggcgc tggcaacgtc tccggcgctg acagatgagc tggtcagcca cggcgagctg     360
atgtcgaccc tgctgtttgt tgagatcctg cgcgaacgcg atgttcaggc acagtggttt     420
gatgtacgta agtgatgcg taccaacgac cgatttggtc gtgcagagcc agatatagcc     480
gcgctggcgg aactggccgc gctgcagctg ctcccacgtc tcaatgaagg cttagtgatc     540
acccagggat ttatcggtag cgaaaataaa ggtcgtacaa cgacgcttgg ccgtggaggc     600
agcgattata cggcagcctt gctggcggag gctttacacg catctcgtgt tgatatctgg     660
accgacgtcc cgggcatcta caccaccgat ccacgcgtag tttccgcagc aaaacgcatt     720
gatgaaatcg cgtttgccga agcggcagag atggcaactt tggtgcaaa agtactgcat     780 ccggcaacgt tgctacccgc agtacgcagc gatatcccgg tctttgtcgg ctccagcaaa     840
gacccacgcg caggtggtac gctggtgtgc aataaaactg aaaatccgcc gctgttccgc     900
gctctggcgc ttcgtcgcaa tcagactctg ctcactttgc acagcctgaa tatgctgcat     960
tctcgcggtt cctcgcgga gttttcggc atcctcgcgc ggcataatat tcggtacgc    1020 ttaatcacca cgtcagaagt gagcgtggca ttaaccttg ataccaccgg ttcaacctcc    1080
actggcgata cgttgctgac gcaatctctg ctgatggagc tttccgcact gtgtcgggtg    1140
gaggtggaag aaggtctggc gctggtcgcg ttgattggca atgacctgtc aaaagcctgc    1200
ggcgttggca agaggtatt cggcgtactg gaaccgttca acattcgcat gatttgttat    1260
ggcgcatcca gccataacct gtgcttcctg gtgcccggcg aagatgccga gcaggtggtg    1320
caaaaactgc atagtaattt gtttgagtaa                                    1350

<210> SEQ ID NO 8
<211> LENGTH: 449
<212> TYPE: PRT
<213> ORGANISM: Artificial sequence
<220> FEATURE:
<223> OTHER INFORMATION: polypeptide

<400> SEQUENCE: 8

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Leu Ala Thr Ser Pro Ala Leu Thr Asp
                100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
                180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
                260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Arg Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415
```

```
Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu
```

<210> SEQ ID NO 9
<211> LENGTH: 55
<212> TYPE: DNA
<213> ORGANISM: Artificial sequence
<220> FEATURE:
<223> OTHER INFORMATION: primer

<400> SEQUENCE: 9
ctagcactag tgaaagagga gaaatactag atgtctgaaa ttgttgtctc caaat      55

<210> SEQ ID NO 10
<211> LENGTH: 30
<212> TYPE: DNA
<213> ORGANISM: Artificial sequence
<220> FEATURE:
<223> OTHER INFORMATION: primer

<400> SEQUENCE: 10
ttactcaaac aaattactat gcagttttg                                   30

<210> SEQ ID NO 11
<211> LENGTH: 60
<212> TYPE: DNA
<213> ORGANISM: Artificial sequence
<220> FEATURE:
<223> OTHER INFORMATION: primer

<400> SEQUENCE: 11
ttgacggcta gctcagtcct aggtacagtg ctagcactag tgaaagagga gaaatactag  60

<210> SEQ ID NO 12
<211> LENGTH: 31
<212> TYPE: DNA
<213> ORGANISM: Artificial sequence
<220> FEATURE:
<223> OTHER INFORMATION: primer

<400> SEQUENCE: 12
gcgtctagat tgacggctag ctcagtccta g                                31

<210> SEQ ID NO 13
<211> LENGTH: 39
<212> TYPE: DNA
<213> ORGANISM: Artificial sequence
<220> FEATURE:
<223> OTHER INFORMATION: primer

<400> SEQUENCE: 13
ggcgagctct tactcaaaca aattactatg cagttttg                         39

<210> SEQ ID NO 14
<211> LENGTH: 40
<212> TYPE: DNA
<213> ORGANISM: Artificial sequence
<220> FEATURE:
<223> OTHER INFORMATION: primer

<400> SEQUENCE: 14
cctcgcgcgg cataatattt cggtaccgtt aatcaccacg                       40

<210> SEQ ID NO 15
<211> LENGTH: 40
<212> TYPE: DNA
<213> ORGANISM: Artificial sequence
<220> FEATURE:
<223> OTHER INFORMATION: primer

<400> SEQUENCE: 15
cgtggtgatt aacggtaccg aaatattatg ccgcgcgagg            40

<210> SEQ ID NO 16
<211> LENGTH: 35
<212> TYPE: DNA
<213> ORGANISM: Artificial sequence
<220> FEATURE:
<223> OTHER INFORMATION: primer

<400> SEQUENCE: 16
cgcggcataa tatttcggta gtcttaatca ccacg                 35

<210> SEQ ID NO 17
<211> LENGTH: 35
<212> TYPE: DNA
<213> ORGANISM: Artificial sequence
<220> FEATURE:
<223> OTHER INFORMATION: primer

<400> SEQUENCE: 17
cgtggtgatt aagactaccg aaatattatg ccgcg                 35

<210> SEQ ID NO 18
<211> LENGTH: 37
<212> TYPE: DNA
<213> ORGANISM: Artificial sequence
<220> FEATURE:
<223> OTHER INFORMATION: primer

<400> SEQUENCE: 18
cgcgcggcat aatatttcgg tacgcttaat caccacg               37

<210> SEQ ID NO 19
<211> LENGTH: 37
<212> TYPE: DNA
<213> ORGANISM: Artificial sequence
<220> FEATURE:
<223> OTHER INFORMATION: primer

<400> SEQUENCE: 19
cgtggtgatt aagcgtaccg aaatattatg ccgcgcg               37

<210> SEQ ID NO 20
<211> LENGTH: 34
<212> TYPE: DNA
<213> ORGANISM: Artificial sequence
<220> FEATURE:
<223> OTHER INFORMATION: primer

<400> SEQUENCE: 20
cgcatgattt gtgctggcgc atccagccat aacc                  34

<210> SEQ ID NO 21
<211> LENGTH: 34
<212> TYPE: DNA
<213> ORGANISM: Artificial sequence
<220> FEATURE:

<223> OTHER INFORMATION: primer

<400> SEQUENCE: 21
ggttatggct ggatgcgcca gcacaaatca tgcg                          34

<210> SEQ ID NO 22
<211> LENGTH: 32
<212> TYPE: DNA
<213> ORGANISM: Artificial sequence
<220> FEATURE:
<223> OTHER INFORMATION: primer

<400> SEQUENCE: 22
cattcgcatg acttgttatg gcgcatccag cc                            32

<210> SEQ ID NO 23
<211> LENGTH: 32
<212> TYPE: DNA
<213> ORGANISM: Artificial sequence
<220> FEATURE:
<223> OTHER INFORMATION: primer

<400> SEQUENCE: 23
ggctggatgc gccataacaa gtcatgcgaa tg                            32

<210> SEQ ID NO 24
<211> LENGTH: 33
<212> TYPE: DNA
<213> ORGANISM: Artificial sequence
<220> FEATURE:
<223> OTHER INFORMATION: primer

<400> SEQUENCE: 24
gtattcggcg tactggaacc ggccaacatt cgc                           33

<210> SEQ ID NO 25
<211> LENGTH: 33
<212> TYPE: DNA
<213> ORGANISM: Artificial sequence
<220> FEATURE:
<223> OTHER INFORMATION: primer

<400> SEQUENCE: 25
gcgaatgttg gccggttcca gtacgccgaa tac                           33

<210> SEQ ID NO 26
<211> LENGTH: 40
<212> TYPE: DNA
<213> ORGANISM: Artificial sequence
<220> FEATURE:
<223> OTHER INFORMATION: primer

<400> SEQUENCE: 26
cctgtcaaaa gcctgcaagg ttggcaaaga ggtattcggc                    40

<210> SEQ ID NO 27
<211> LENGTH: 40
<212> TYPE: DNA
<213> ORGANISM: Artificial sequence
<220> FEATURE:
<223> OTHER INFORMATION: primer

<400> SEQUENCE: 27
gccgaatacc tctttgccaa ccttgcaggc ttttgacagg                    40

ASPARAGINIC ACID KINASE III MUTANT AND HOST CELLS AND USE THEREOF

TECHNICAL FIELD

The present invention relates to the field of biotechnology. More specifically, the present invention relates to aspartokinase III (abbreviated as AK III, also known as LysC) mutant and uses thereof.

BACKGROUND

L-lysine is the most important essential amino acid as nutrients for human and animal, and plays a very important role in the food industry, breeding industry and feed industry. In recent years, the market demand for L-lysine has steadily increased, and the volume of sales of L-lysine on the world market is more than one million tons. Currently, lysine is mainly produced by microorganism fermentation.

In many microorganisms, L-lysine is synthesized by using aspartic acid as the precursor, including two steps in common with some amino acids, such as methionine and threonine. In *E. coil*, the biosynthesis pathway for L-lysine includes a nine-step enzymatic process (indicated by the following scheme), wherein the first-step reaction of lysine biosynthesis catalyzed by aspartokinase is the rate-limiting step of lysine production, and the activity of aspartokinase determines the ratio of metabolic flux to L-lysine synthetic pathway. In *E. coli*, there are 3 aspartokinases, named as aspartokinase I (AK I, encoded by the thrA gene), aspartokinase II (AK II, encoded by the metL gene), aspartokinase III (AK III, encoded by the lysC gene, and the nucleotide sequence of the encoding gene is represented by SEQ ID NO: 1, and the amino acid sequence thereof is represented by SEQ ID NO: 2), respectively. AK I and AK II are both bifunctional enzymes which further possess homoserine dehydrogenase activity. AK I is inhibited by threonine and lysine feedback on the enzyme activity level, and AK III is inhibited by lysine (the final product) feedback on the enzyme activity level (Bearer C F, Neet K E; Stadtman, E R, Cohen, G N, LeBras, G., Robichon-Szulmajster, H. (1961). "Feed-back Inhibition and Repression of Aspartokinase Activity in *Escherichia coli* and *Saccharomyces cerevisiae*." J. Biol. Chem.). AK II is not inhibited by the feedback of amino acids in the aspartate family on the enzyme activity level, but it is strictly regulated on the transcription level (X Dong, P J Quinn, X Wang. (2011). "Metabolic engineering of *Escherichia coli* and *Corynebacterium glutamicum* for the production of L-threonine. "Biotechnology advances).

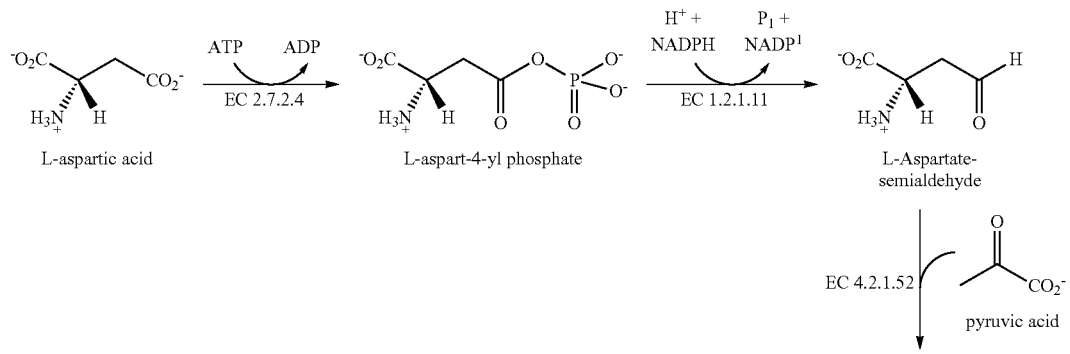

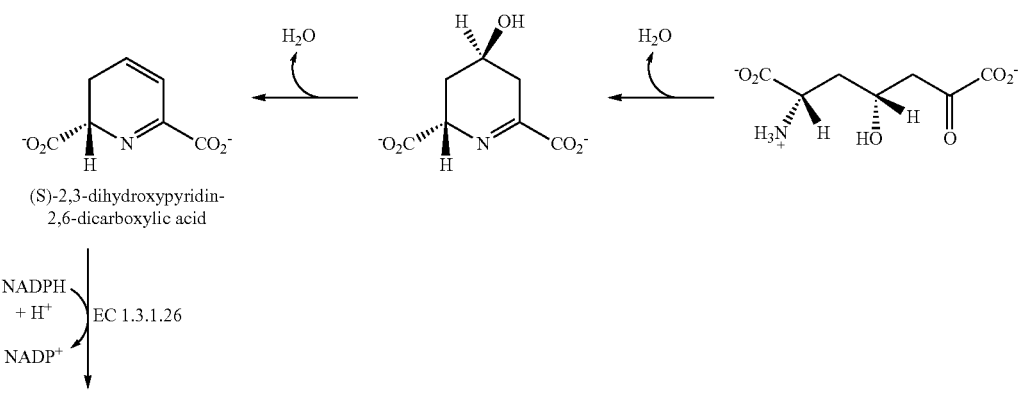

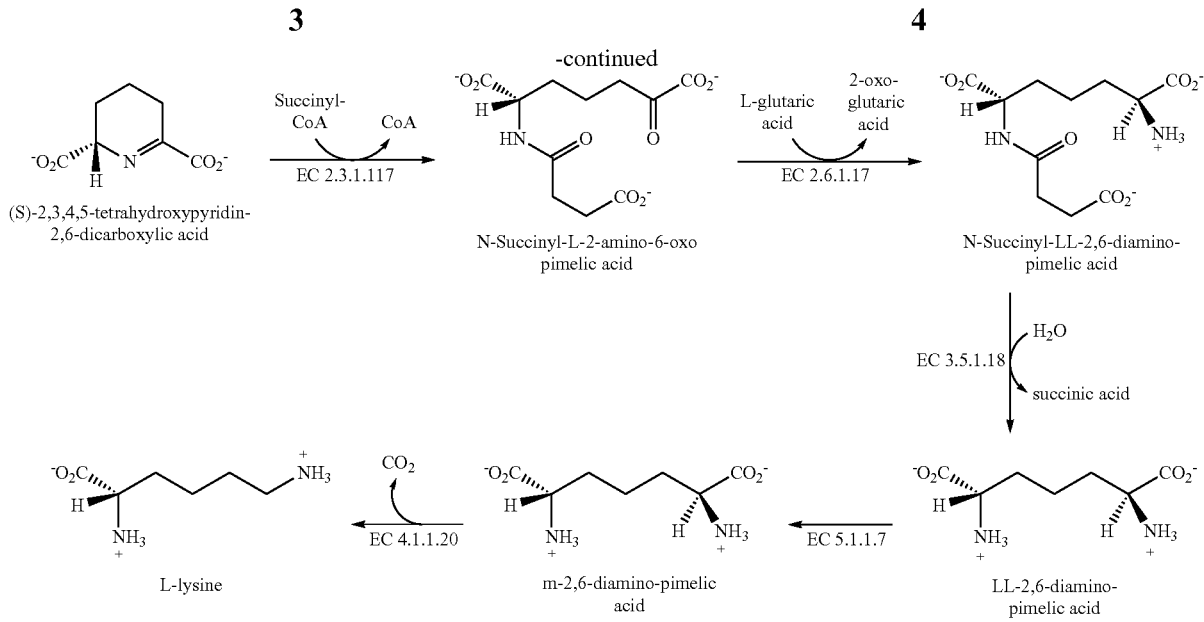

Biosynthetic Pathway from Aspartate to L-lysine

At present, *E. coli* has been modified by many enterprises for the industrial production of lysine. Since the activity of aspartokinase is strictly regulated by lysine, eliminating lysine feedback inhibition on aspartokinase is an inevitable approach to develop high-yield strains of lysine. Two AK III mutants which have feedback inhibition eliminated are obtained by DuPont through random mutation screen, and in said mutants, 352 threonine is replaced by isoleucine (T352I) and 318 methionine is replaced by isoleucine (M318I), respectively (EP1394257). Ajinomoto Company (Japan) also obtained AK III mutants which have lysine feedback inhibition partly eliminated (US005661012, US2010190216, US2010173368).

Additionally, since aspartokinase is the enzyme shared by the synthetic pathways for L-lysine, L-threonine and L-methionine, for example, Chinese patent CN 1071378C disclosed an aspartokinase with its feedback inhibition eliminated and methods for producing L-lysine by using this kinase and host cells comprising the same. If an aspartokinase, which has high specific-activity and L-lysine feedback inhibition effectively eliminated, could be obtained, it will be of great significance for producing L-lysine, L-threonine and L-methionine, and even for other metabolites using L-threonine as precursor, including L-isoleucine and L-valine.

Summing up, there is an urgent need in the art for aspartokinase mutants which have high enzymatic activity and L-lysine feedback inhibition effectively eliminated.

SUMMARY OF THE INVENTION

The object of the present invention is to provide AK III mutants which have high enzyme activity and eliminated L-lysine feedback inhibition, and uses of such mutants as well as methods for using such mutants.

In the first aspect, the present invention provides an aspartokinase, the amino acid sequence of said aspartokinase having an amino acid residue which is not aspartic acid at the position corresponding to position 340 in the amino acid sequence of SEQ ID NO: 2.

In a preferred embodiment, the aspartokinase is derived from *Escherichia* bacteria, preferably derived from *Escherichia coli*.

In a preferred embodiment, the aspartokinase:
a). has the amino acid sequence of SEQ ID NO: 2 and the amino acid residue at position 340 is not aspartic acid, or
b). is derived from a), wherein the aspartokinase has a sequence formed through substitution, deletion or addition of one or several amino acid residues, preferably 1-20, more preferably 1-15, more preferably 1-10, more preferably 1-3, most preferably 1 amino acid residue from the sequence defined in a), and essentially has the function of the aspartokinase defined in a).

In a preferred embodiment, the amino acid sequence of said aspartokinase has an amino acid residue at the position corresponding to position 340 in the amino acid sequence of SEQ ID NO: 2 which is at least one selected from the following amino acids: Pro, Ala, Arg, Lys, Gln, Asn, Val, Ile, Leu, Met and Phe.

In a further preferred embodiment, the amino acid sequence of said aspartokinase has an amino acid residue at the position corresponding to position 340 in the amino acid sequence of SEQ ID NO: 2 which is selected from Pro, Arg or Val.

In a preferred embodiment, the aspartokinase:
a). has the amino acid sequence of SEQ ID NO: 4, 6 or 8; or
b). is derived from a), wherein the aspartokinase comprises a sequence formed through substitution, deletion or addition of one or several amino acid residues, preferably 1-20, more preferably 1-15, more preferably 1-10, more preferably 1-3, most preferably 1 amino acid residue from the sequence defined in a), and essentially has the function of the aspartokinase defined in a).

In a further preferred embodiment, the amino acid sequence of aspartokinase is shown in SEQ ID NO: 4, 6 or 8.

In a preferred embodiment, the lysine feedback inhibition of said aspartokinase is eliminated.

In another preferred embodiment, in the presence of L-lysine at the concentration of 10 mM, said aspartokinase retains at least 20% of the activity; preferably, at least 30%-40% of the activity; more preferably, at least 50%-60% of the activity; more preferably, at least 70%-80% of the activity; and most preferably, at least 90% of the activity.

In a further preferred embodiment, in the presence of L-lysine at the concentration of 20 mM, said aspartokinase retains at least 20% of the activity; preferably, at least 30%-40% of the activity; more preferably, at least 50%-60% of the activity; more preferably, at least 70% of the activity; and most preferably, at least 80% of the activity.

In a further preferred embodiment, in the presence of L-lysine at the concentration of 100 mM, said aspartokinase retains at least 20% of the activity; preferably, at least 30%-40% of the activity; more preferably, at least 50%-60% of the activity; more preferably, at least 70% of the activity; and most preferably, at least 80% of the activity.

In the second aspect, the present invention provides a gene encoding the aspartokinase according to the first aspect of the present invention.

In a preferred embodiment, the nucleotide sequence of said gene is shown in SEQ ID NO: 3, 5 or 7.

In the third aspect, the present invention provides a vector comprising the encoding gene according to the second aspect of the present invention.

In the fourth aspect, the present invention provides a host cell comprising the encoding gene according to the second aspect of the present invention.

In a preferred embodiment, the amino acid sequence of said aspartokinase has an amino acid residue at the position corresponding to position 340 in the amino acid sequence of SEQ ID NO: 2 which is at least one selected from the following amino acids: Pro, Ala, Arg, Lys, Gln, Asn, Val, He, Leu, Met and Phe.

In a further preferred embodiment, the amino acid sequence of said aspartokinase has an amino acid residue at the position corresponding to position 340 in the amino acid sequence of SEQ ID NO: 2 which is selected from Pro, Arg or Val.

In a preferred embodiment, the aspartokinase:
a). has the amino acid sequence of SEQ ID NO: 4, 6 or 8; or
b). is derived from a), wherein the aspartokinase has a sequence formed through substitution, deletion or addition of one or several amino acid residues, preferably 1-20, more preferably 1-15, more preferably 1-10, more preferably 1-3, most preferably 1 amino acid residue from the sequence defined in a), and essentially has the function of the aspartokinase defined in a).

In another preferred embodiment, the nucleotide sequence of said gene is shown in SEQ ID NO: 3, 5 or 7.

In a preferred embodiment, said host cell is from the genus *Escherichia, Corynebacterium, Brevibacterium* sp., *Bacillus, Serratia*, or *Vibrio*.

In a further preferred embodiment, said host cell is *Escherichia coli* (*E. Coli*) or *Corynebacterium glutamicum*.

In a preferred embodiment, said host cell has the encoding gene according to the second aspect of the invention integrated into its chromosomal, or said host cell comprises the vector according to the third aspect of the present invention.

In a preferred embodiment, said host cell expresses the aspartokinase according to the present invention.

In another preferred embodiment, one or more genes selected from the following group are attenuated or the expression thereof is reduced in said host cell:
a. adhE gene encoding alcohol dehydrogenase;
b. ackA gene encoding acetate kinase;
c. pta gene encoding phosphate acetyltransferase;
d. ldhA gene encoding lactate dehydrogenase;
e. focA gene encoding formate transporter;
f. pflB gene encoding pyruvate formate lyase;
g. poxB gene encoding pyruvate oxidase;
h. thrA gene encoding aspartokinase I/homoserine dehydrogenase I bifunctional enzyme;
i. thrB gene encoding homoserine kinase;
j. ldcC gene encoding lysine decarboxylase; and
h. cadA gene encoding lysine decarboxylase.

In another preferred embodiment, one or more genes selected from the following group are enhanced or overexpressed in said host cell:
a. dapA gene encoding dihydrodipicolinate synthase for eliminating lysine feedback inhibition;
b. dapB gene encoding dihydrodipicolinate reductase;
c. ddh gene encoding diaminopimelate dehydrogenase;
d. dapD encoding tetrahydrodipicolinate succinylase and dapE encoding succinyl diaminopimelate deacylase;
e. asd gene encoding aspartate-semialdehyde dehydrogenase;
f. ppc gene encoding phosphoenolpyruvate carboxylase; or
g. pntAB gene encoding nicotinamide adenine dinucleotide transhydrogenase.

In the fifth aspect, the present invention provides use of the host cell according to the fourth aspect of the present invention in the production of L-amino acid.

In the sixth aspect, the present invention provides a method for producing L-amino acid, said method comprising the following steps:
a). culturing the host cell of claim 4 to produce L-amino acid; and
b). separating L-amino acid from the culture.

In a preferred embodiment, the method is performed at 30-45° C., preferably at 37° C.

In the seventh aspect, the present invention provides use of the aspartokinase according to the first aspect of the present invention in the production of L-amino acids.

In preferred embodiments according to the sixth aspect and the seventh aspect of the present invention, L-amino acids are L-lysine, L-threonine, L-methionine, L-isoleucine, or L-valine.

In the eighth aspect, the present invention provides a method for producing L-lysine, L-threonine, L-methionine, L-isoleucine or L-valine, said method comprising the following steps:
a). using the aspartokinase (EC 2.7.2.4) according to the first aspect of the present invention to catalyze the following reaction during the process of producing L-lysine, L-threonine, L-methionine, L-isoleucine or L-valine from L-aspartic acid, so as to obtain L-lysine, L-threonine, L-methionine, L-isoleucine, or L-valine,

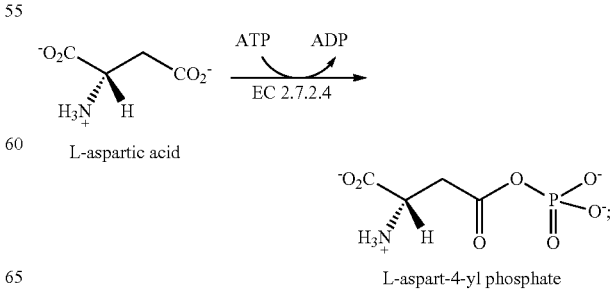

and b). isolating L-lysine, L-threonine, L-methionine, L-isoleucine, or L-valine from the above reaction system.

In the ninth aspect, the present invention provides a method for preparing the aspartokinase according to the first aspect of the present invention, said method comprising the following steps:

a). modifying the encoding sequence for the amino acid sequence of SEQ ID NO: 2 such that the encoded amino acid sequence has an amino acid residue at the position corresponding to position 340 in the amino acid sequence of SEQ ID NO: 2 that is mutated to an amino acid other than aspartic acid;

b). using the encoding sequence obtained in a) to directly transfect suitable host cells or introducing said encoding sequence into suitable host cells via a vector;

c). culturing the host cells obtained in b);

d). isolating the aspartokinase produced by said host cells from the culturing system obtained in step c); and e). determining the ability of said aspartokinase to eliminate lysine feedback inhibition.

In a preferred embodiment, the amino acid sequence of said aspartokinase has an amino acid residue at the position corresponding to position 340 in the amino acid sequence of SEQ ID NO: 2 which is at least one selected from the following amino acids: Pro, Ala, Arg, Lys, Gln, Asn, Val, Ile, Leu, Met and Phe.

In a further preferred embodiment, the amino acid sequence of said aspartokinase has an amino acid residue at the position corresponding to position 340 in the amino acid sequence of SEQ ID NO: 2 which is selected from Pro, Arg or Val.

In the tenth aspect of the present invention, the present invention provides a method for modifying wild-type aspartokinase to eliminate lysine feedback inhibition, said method comprising the following steps:

a). aligning the amino acid sequence of wild-type aspartokinase with the amino acid sequence of SEQ ID NO: 2; and b). modifying the encoding sequence for the wild-type aspartokinase such that the encoded amino acid sequence has an amino acid residue at the position corresponding to position 340 in the amino acid sequence of SEQ ID NO: 2 that is mutated to an amino acid other than aspartic acid;

c). using the encoding sequence obtained in b) to directly transfect suitable host cells or introducing said encoding sequence into suitable host cells via a vector;

d). culturing the host cells obtained in c);

e). isolating the aspartokinase produced by said host cells from the culturing system obtained in step d); and f). determining the ability of said aspartokinase to eliminate lysine feedback inhibition.

In a preferred embodiment, the amino acid sequence of said aspartokinase has an amino acid residue at the position corresponding to position 340 in the amino acid sequence of SEQ ID NO: 2 which is at least one selected from the following amino acids: Pro, Ala, Arg, Lys, Gln, Asn, Val, Ile, Leu, Met, and Phe.

In a further preferred embodiment, the amino acid sequence of said aspartokinase has an amino acid residue at the position corresponding to position 340 in the amino acid sequence of SEQ ID NO: 2 which is selected from Pro, Arg, or Val.

It should be understood that in the present invention, the technical features specifically described above and below (such as in the Examples) can be combined with each other, thereby constituting a new or preferred technical solution which needs not be described one by one.

MODES FOR CARRYING OUT THE INVENTION

Figure 1:
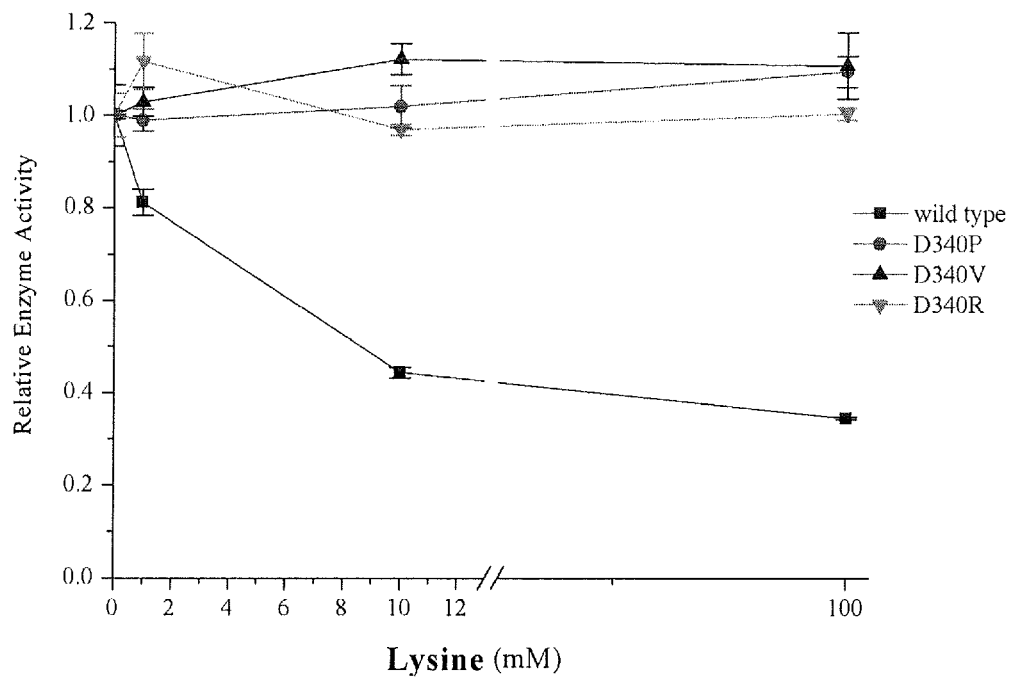
FIG. 1 shows the comparison of relative enzyme activity between the crude enzyme solution containing AK III mutant according to the present invention and that containing wild-type AK III.

After extensive and intensive studies, the inventors have unexpectedly discovered that aspartokinase III derived from *E. coli* can be genetically engineered at position 340, and the obtained aspartokinase III mutant not only has excellent enzyme activity, but also has its L-lysine feedback inhibition effectively eliminated; the mutant, therefore, can be used for high-efficient production of L-lysine. The present invention was thus completed based on the above discovery.

Aspartokinase According to the Present Invention

As used herein, the term "aspartokinase according to the present invention" and "polypeptide according to the present invention" can be used interchangeably, and will have the meaning as commonly understood by a skilled person in the art. The aspartokinase according to the present invention has the activity for transferring phosphate group to aspartic acid.

In a specific embodiment, the amino acid sequence of the aspartokinase according to the present invention has an amino acid residue which is not aspartic acid at the position corresponding to position 340 in the amino acid sequence of SEQ ID NO: 2.

In a preferred embodiment, the amino acid sequence of the aspartokinase according to the present invention has an amino acid residue at the position corresponding to position 340 in the amino acid sequence of SEQ ID NO: 2 which is at least one selected from the following amino acids: Pro, Ala, Arg, Lys, Gln, Asn, Val, Ile, Leu, Met, and Phe.

In a preferred embodiment, the amino acid sequence of the aspartokinase according to the present invention has an amino acid residue at the position corresponding to position 340 in the amino acid sequence of SEQ ID NO: 2 which is selected from Pro, Arg, or Val.

In a preferred embodiment, the aspartokinase according to the present invention:

(a). has the amino acid sequence of SEQ ID NO: 4, 6 or 8; or (b). is derived from a), wherein the aspartokinase has a sequence formed through substitution, deletion or addition of one or several amino acid residues, preferably 1-20, more preferably 1-15, more preferably 1-10, more preferably 1-3, most preferably 1 amino acid residue from the sequence defined in (a), and essentially has the function of the aspartokinase defined in (a).

In a specific embodiment, in the presence of L-lysine at a concentration of higher than 10 mM, preferably higher than 20 mM, most preferably higher than 100 mM, the aspartokinase according to the present invention can effectively eliminate lysine feedback inhibition.

It will be readily known to a person skilled in the art that, a few amino acid residues in certain regions, e.g., non-important region, of a polypeptide can be changed without substantially altering biological activities. For example, appropriately replacing some amino acids in a sequence won't affect its activity (See Watson et al., Molecular Biology of The Gene, Fourth Edition, 1987, The Benjamin/Cummings Pub. Co. P224). Accordingly, a person skilled in the art can perform such replacement and ensure that the resulting molecule still has the desired biological activity.

Therefore, the polypeptide of the present invention can be further mutated in addition to its non-aspartic acid at the position corresponding to position 340 in the amino acid sequence of SEQ ID NO: 2, while still having the function and activity of the aspartokinase according to the present invention. For example, the aspartokinase according to the present invention (a). has the amino acid sequence of SEQ ID NO: 4, 6 or 8; or b) is derived from a), wherein the aspartokinase has a sequence formed through substitution, deletion or addition of one or several amino acid residues, preferably 1-20, more preferably 1-15, more preferably 1-10, more preferably 1-3, most preferably 1 amino acid residue from the sequence defined in (a), and essentially has the function of the aspartokinase defined in (a).

In the present invention, the aspartokinase according to the present invention includes the mutants formed by replacing at most 20, preferably at most 10, more preferably at most 3, more preferably at most 2, most preferably at most 1 amino acid replaced with an amino acid of similar properties when compared with the aspartokinase having the amino acid sequence of SEQ ID NO: 4, 6 or 8. These mutants with conservative variations may be generated through amino acid replacements as shown in, for example the following table.

| Initial residue | Representative residues for replacement | Preferred residues for replacement |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide encoding the polypeptide of the present invention. The term "polynucleotide encoding a polypeptide" may include a polynucleotide encoding such polypeptide, and may further include a polynucleotide with additional coding and/or non-coding sequences.

Thus, as used herein, "comprise", "have" or "include" includes "comprise", "mainly consisting of . . . ", "essentially consisting of . . . " and "consisting of . . . "; and "mainly mainly consisting of . . . ", "essentially consisting of . . . " and "consisting of . . . " are lower-level concepts of "comprise", "have" or "include".

Amino Acid Residue at the Position Corresponding to Position 340 in the Amino Acid Sequence of SEQ ID NO: 2

A person skilled in the art will know that some amino acid residues in the amino acid sequence of a protein can be mutated in many ways, for example substituted, added or deleted, and the resulting mutants whereas can still have the function or activity of the original protein. Therefore, the amino acid sequences specifically disclosed in the present invention can be changed by a person skilled in the art, and the mutants obtained may still have the desired activity. In this situation, the position in the mutant which corresponds to position 340 in the amino acid sequence of SEQ ID NO: 2 may not be position 340, but the mutants thus obtained still fall within the scope of the present invention.

As used herein, the term "correspond to" has the meaning as commonly understood by a skilled person in the art. Specifically, "correspond to" indicates that, upon sequence homology or sequence identity alignment between two sequences, a position in one sequence corresponds to a specified position in the other sequence. Therefore, in respect of "the amino acid residue at the position corresponding to position 340 in the amino acid sequence of SEQ ID NO: 2", if a 6-His tag is added at one end of the amino acid sequence of SEQ ID NO: 2, the position in the resulting mutant corresponding to position 340 in the amino acid sequence of SEQ ID NO: 2 may be position 346; and if a few amino acid residues are deleted from the amino acid sequence of SEQ ID NO: 2, the position in the resulting mutant corresponding to position 340 in the amino acid sequence of SEQ ID NO: 2 may be position 338; and the like. For another example, if a sequence having 400 amino acid residues possesses high homology or sequence identity with positions 20-420 in the amino acid sequence of SEQ ID NO: 2, the position in the resulting mutant corresponding to position 340 in the amino acid sequence of SEQ ID NO: 2 may be position 320.

In a specific embodiment, the homology or sequence identity can be 80% or higher, more preferably 90% or higher, more preferably 95%-98%, most preferably 99% or higher.

Methods for determining sequence homology or identity as commonly known to a person skilled in the art include, but not limited to: Computational Molecular Biology, Lesk, A M, eds., Oxford University Press, New York, 1988; Biocomputing: Informatics and Genome Projects, Smith, D W, eds., Academic Press, New York, 1993; Computer Analysis of Sequence Data, $1^{st}$ part, Griffin, AM, and Griffin, H G. eds., Humana Press, New Jersey, 1994; Sequence Analysis in Molecular Biology, von Heinje, G, Academic Press, 1987, and Sequence Analysis Primer, Gribskov, M and Devereux., J. eds., M Stockton Press, New York, 1991, and Carillo, H and Lipman, D., SIAM J. Applied Math, 48: 1073 (1988). A preferred method for determining identity should obtain the maximum match between tested sequences. The methods for determining identity are compiled in publicly available computer programs. Preferred computer program methods for determining identity between two sequences include, but are not limited to: GCG package (Devereux, J, et al., 1984), BLASTP, BLASTN and FASTA (Altschul, S, F et al., 1990). The BLASTX program (BLAST Manual, Altschul, S, et al., NCBI NLM NIH Bethesda, Md. 20894; Altschul, S et al., 1990.) is publicly available from NCBI and other sources. The well-known Smith Waterman algorithm can also be used to determine identity.

Host Cells

As used herein, the term "host cell" has the same meaning as commonly understood by a person skilled in the art, i.e., a host cell which is capable of generating the aspartokinase according to the present invention. In other words, any host cell can be used in the present invention, as long as the aspartokinase according to the present invention can be expressed in the host cell.

For example, in a specific example, a host cell comprising an exogenous gene encoding the aspartokinase according to the present invention, preferably an AK-deficient *E. coli* strain, is used in the present invention. However, a person skilled in the art will understood that the present invention is not limited to the host cell comprising an exogenous encoding gene. For example, the aspartokinase-encoding gene contained in the host cell of the present invention can not only be a recombinant vector or plasmid, it can also be integrated into genome, that is, the enzyme-encoding gene integrated into genome can be obtained through homologous recombination of a transferred plasmid, or can be obtained through site-directed mutation of relevant sites on genome.

In a specific embodiment, the host cell of the present invention can produce L-amino acids with high efficiency, and resist L-lysine feedback inhibition.

In a specific embodiment, the host cell of the present invention is capable of producing L-lysine, L-threonine, L-methionine, L-isoleucine or L-valine.

In a specific embodiment, the amino acid sequence of said aspartokinase has an amino acid residue at the position corresponding to position 340 in the amino acid sequence of SEQ ID NO: 2 which is at least one selected from the following amino acids: Pro, Ala, Arg, Lys, Gln, Asn, Val, Ile, Leu, Met, and Phe.

In a preferred embodiment, the amino acid sequence of said aspartokinase has an amino acid residue at the position corresponding to position 340 in the amino acid sequence of SEQ ID NO: 2 which is selected from Pro, Arg, or Val.

In a preferred embodiment, said aspartokinase:
(a). has the amino acid sequence of SEQ ID NO: 4, 6 or 8; or
(b). is derived from a), wherein the aspartokinase has a sequence formed through substitution, deletion or addition of one or more amino acid residues from the sequence defined in (a), and essentially has the function of the aspartokinase defined in (a).

In a preferred embodiment, the nucleotide sequence of said gene is shown in SEQ ID NO: 3, 5 or 7.

In a preferred embodiment, said host cell is from the genus *Escherichia, Corynebacterium, Brevibacterium* sp., *Bacillus, Serratia*, or *Vibrio*.

In a preferred embodiment, said host cell is *Escherichia coli* (*E. Coli*) or *Corynebacterium glutamicum*.

In a preferred embodiment, in said host cell, one or more genes selected from the following group are attenuated or the expression thereof is reduced:
a. adhE gene encoding alcohol dehydrogenase;
b. ackA gene encoding acetate kinase;
c. pta gene encoding phosphate acetyltransferase;
d. ldhA gene encoding lactate dehydrogenase;
e. focA gene encoding formate transporter;
f. pflB gene encoding pyruvate formate lyase;
g. poxB gene encoding pyruvate oxidase;
h. thrA gene encoding aspartokinase I/homoserine dehydrogenase I bifunctional enzyme;
i. thrB gene encoding homoserine kinase;
j. ldcC gene encoding lysine decarboxylase; and
h. cadA gene encoding lysine decarboxylase.

Furthermore, a person skilled in the art will understand that, for the production of L-lysine, enhancement or overexpression of one or more enzymes in particular biosynthetic pathways, glycolysis, anaplerotic metabolism in a cell will be beneficial. Therefore, in some embodiments, besides the genes described in the present invention, other relevant genes can be enhanced or overexpressed. For example, one or more genes selected from the following group are enhanced or overexpressed:
a. dapA gene encoding dihydrodipicolinate synthase for eliminating lysine feedback inhibition (EP 1477564);
b. dapB gene encoding dihydrodipicolinate reductase (EP1253195);
c. ddh gene encoding diaminopimelate dehydrogenase (EP1253195);
d. dapD encoding tetrahydrodipicolinate succinylase and dapE encoding succinyl diaminopimelate deacylase (EP1253195);
e. asd gene encoding aspartate-semialdehyde dehydrogenase (EP1253195);
f. ppc gene encoding phosphoenolpyruvate carboxylase (EP 1253195); or
g. pntAB gene encoding nicotinamide adenine dinucleotide transhydrogenase (EP1253195).

Furthermore, for the convenience of experimentation, a mutant strain with inactivated aspartokinase is used in the present invention for testing the enzyme activity and ability to eliminate lysine feedback inhibition of the aspartokinase mutant according to the present invention. However, a person skilled in the art should understand that a natural strain without its aspartokinase being inactivated can also be used in the present invention for testing the enzyme activity and ability to eliminate lysine feedback inhibition of the aspartokinase mutant according to the present invention, as long as a control is set for the experiment.

Use of the Polypeptide or Host Cells of the Invention

The polypeptide of the present invention can be used as an aspartokinase to catalyze the following reaction during the process of producing L-lysine from L-aspartic acid, thereby obtaining L-lysine:

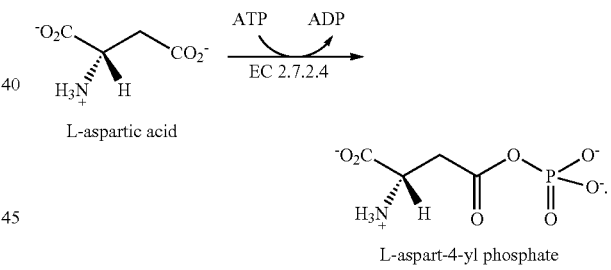

Furthermore, a person skilled in the art has already known that aspartokinase is the enzyme used in the common biosynthetic pathway for L-lysine, L-threonine, and L-methionine and for synthesizing L-isoleucine and L-valine from L-threonine. Accordingly, a person skilled in the art will readily understand that the polypeptide or host cell of the present invention can be used not only to produce L-lysine, but also to produce L-threonine, L-methionine, L-isoleucine and L-valine in view of the teachings of the present invention in combination with the prior art.

Furthermore, a person skilled in the art will readily understand that L-aspartyl-4-phosphate, which is the intermediate produced at a high level by the aspartokinase of the present invention, can also be isolated for producing various downstream products, such as L-threonine, L-methionine, L-isoleucine, and L-valine.

In a specific embodiment, L-lysine can be produced by the host cell of the present invention at 30-45° C., preferably 37° C.

Eliminating Lysine Feedback Inhibition

A person skilled in the art will understand that, as used herein, the term "eliminating lysine feedback inhibition" means that an enzyme originally subject to lysine feedback inhibition is modified to reduce the degree of lysine feedback inhibition. Such reduction is obtained by comparing the degree of inhibition between two enzymes under the same lysine concentration. "Eliminating lysine feedback inhibition" includes partially or totally eliminating feedback inhibition. The degree of inhibition means the ratio of activity loss (i.e., being inhibited) for aspartokinase in the presence of a certain concentration of lysine when compared with that in the absence of lysine. Under such condition, the ratio of the retained aspartokinase activity is named as ratio of residual enzyme activity or ratio of retained enzyme activity or relative enzyme activity.

Since ratio of enzyme activity loss+ratio of residual enzyme activity=100%, the degree of inhibition is usually represented by the ratio of residual enzyme activity. The higher the ratio of residual enzyme activity, the lower the degree of inhibition. Accordingly, "eliminating lysine feedback inhibition" is generally depicted by the comparison between the two ratios of residual enzyme activity before and after the modification.

In a particular embodiment, in the presence of 10 mM L-lysine, aspartokinase of the present invention retains at least 20% of the activity, thus having the lysine feedback inhibition eliminated in comparison with the wild-type aspartokinase; preferably, retains at least 30-40% of the activity; more preferably, at least 50%-60% of the activity; more preferably, at least 70%-80% of the activity; more preferably, at least 90% of the activity.

In a preferred embodiment, in the presence of 20 mM L-lysine, aspartokinase of the present invention retains at least 20% of the activity, thus having the lysine feedback inhibition eliminated in comparison with the wild-type aspartokinase; preferably, retains at least 30-40% of the activity; more preferably, retains at least 50%-60% of the activity; more preferably, retains at least 70% of the activity; more preferably, retains at least 80% of the activity.

In a preferred embodiment, in the presence of 100 mM L-lysine, aspartokinase of the present invention retains at least 20% of the activity, thus having the lysine feedback inhibition eliminated in comparison with the wild-type aspartokinase; preferably, retains at least 30-40% of the activity; more preferably, retains at least 50%-60% of the activity; more preferably, retains at least 70% of the activity; more preferably, retains at least 80% of the activity.

Enhancement/Attenuation

As used herein, the term "enhancement" or "enhance" refers to the increase of intracellular activity of one or more enzymes encoded by DNA in a microorganism, including but not limited to, by increasing the copy number of the encoding genes, enhancing the strength of transcription or translation, or using a gene or allele encoding an enzyme with increased activity, and optionally combinations thereof.

As used herein, the term "attenuation" or "attenuate" refers to the decrease or elimination of intracellular activity of one or more enzymes encoded by DNA in a microorganism, including but not limited to, by deleting part or all of the encoding genes, frameshift mutation of gene reading frame, weakening the strength of transcription or translation, or using a gene or allele encoding an enzyme or protein with lower activity, and optionally combinations thereof.

Immobilized Enzyme

As used herein, the term "immobilized enzyme" has the meaning commonly understood by a person skilled in the art. In particular, the term means that a water-soluble enzyme, upon treatment by physical or chemical means, binds to a water-insoluble macromolecular carrier conjugate or is entrapped therein, so that the enzyme is present in a water insoluble gel or microcapsules of semipermeable membrane, thereby reducing the mobility of the enzyme.

An immobilized enzyme still has enzyme activity, and can act in solid phase on substrates in a catalytic reaction. Upon immobilization, an enzyme generally has increased stability, is easily separated from the reaction system, easily to be controlled, can be used repeatedly, easily to be transported and stored, and conducive to automatic production. As an enzyme application technology, immobilized enzyme was developed in the past decade, and has attractive prospects in industrial production, chemical analysis and medicine.

Based on the teachings herein, the aspartokinase of the present invention can be readily made into immobilized enzyme by a person skilled in the art, which, in turn, can be used to catalyze the reaction from aspartic acid to L-lysine, thereby efficiently producing L-lysine and effectively eliminating lysine feedback inhibition.

Uses and Advantages of the Invention

1. Various aspartokinases, encoding genes thereof and host cells comprising the encoding genes provided in the invention can be used in industry to produce L-lysine and other amino acids;

2. Various aspartokinases provided in the invention are aspartokinases which have high specific activity and can effectively eliminate L-lysine feedback inhibition. Accordingly, various aspartokinases, the encoding genes thereof and host cells comprising the encoding genes according to the invention can not only efficiently produce L-lysine, but also can effectively eliminate lysine feedback inhibition, thereby possessing broad application prospects in industry;

3. Various aspartokinases and the encoding genes thereof provided in the invention are helpful to clarify and understand L-lysine biosynthesis pathway and the underlying mechanism of feedback inhibition, thereby further providing theoretical foundation and materials for genetic engineering related proteins or host cells.

The invention will be further illustrated with reference to the following specific examples. It is to be understood that these examples are only intended to illustrate the invention, but not to limit the scope of the invention. For the experimental methods in the following examples without particular conditions, they are performed under routine conditions, such as conditions described in Sambrook et al., Molecular Cloning: A Laboratory Manual, New York: Cold Spring Harbor Laboratory Press, 1989, or as instructed by the manufacturer.

EXAMPLE 1

Obtaining AK III Mutants

1. Cloning of the Wild-type AK III Gene

*E.coli* MG1655 (obtained from ATCC 700926, see Blattner F R, et al., The complete genome sequence of *Escherichia coli* K-12 Science 277: 1453-62 (1997)) was cultured in LB medium (tryptone 10 g/L, yeast extract 5 g/L, sodium chloride 10 g/L, pH 7.0) for 12-16 h, at 37° C. and 200 rpm. Cells were collected, and genomic DNAs were extracted by using Biomiga genome extraction kit. Wild-type lysC gene, in front of which a constitutive promoter and suitable SD sequence were added, was obtained through 3 cycles of PCR using E. coli genome as template, appropriate restriction sites were added at both ends of the fragment.

In particular:

The first cycle of PCR: CTAGCACTAGTGAAAGAG-GAGAAATACTAGATGTCTGAAATTGTTGTCTC-CAAAT (SEQ ID NO: 9) and TTACTCAAACAAATTAC-TATGCAGTTTTTG (SEQ ID NO: 10) were used as primers, lysC gene (the encoding gene of wild type lysC, the amino acid sequence thereof is SEQ ID NO: 2, the nucleotide sequence thereof is SEQ ID NO: 1) was amplified from E.coli MG1655 genomic DNA; then the second cycle of PCR was performed by using PCR products from the first cycle of PCR as template and TTGACGGCTAGCTCA-GTCCTAGGTACAGTGCTAGCACTAGTGAAAGAG-GAGAAATACTAG (SEQ ID NO: 11) and TTACT-CAAACAAATTACTATGCAGTTTTTG (SEQ ID NO: 10) as primers; and then the third cycle of PCR was performed by using PCR products from the second cycle of PCR as template and GCGTCTAGATTGACGGCTAGCTCAGTC-CTAG (SEQ ID NO: 12) and GGCGAGCTCTTACT-CAAACAAATTACTATGCAGTTTTTG (SEQ ID NO: 13) as primers; and finally, DNA fragments with XbaI and SacI restriction sites were obtained. The finally obtained DNA fragments were cloned into pWSK29 plasmid by using XbaI and SacI, and the resulting plasmid was named as pWSK29-lysC.

2. Site-directed Mutation of AK III

Mutation sites were introduced into the plasmid pWSK29-lysC through PCR by using Stratagene QuikChange®XL-II site-directed mutagenesis kit and primers D340P-F/D340P-R (see Table 1). The resulting plasmids were recovered from the PCR products by removing enzymes in the PCR system and salt ions in the buffer and then being digested with DpnI for 1 h to remove methylated template plasmid DNAs. The plasmids thus treated were transferred into competent cells Tran10 (purchased from Transgen Biotech., Beijing). The obtained plasmid with the correct mutations was named as pSLL1. The nucleotide sequence of the lysC mutant carried by this plasmid is shown in SEQ ID NO: 3, and the translated amino acid sequence is shown in SEQ ID NO: 4.

Then mutation sites were introduced into the plasmid pWSK29-lysC through PCR by using primers D340V-F/D340V-R (see Table 1). The resulting plasmids were recovered from the PCR products by removing enzymes in the PCR system and salt ions in the buffer and then being digested with DpnI for 1 h to remove methylated template plasmid DNAs. The plasmids thus treated were transferred into competent cells Tran10. The obtained plasmid with the correct mutations was named as pSLL2. The nucleotide sequence of the lysC mutant carried by this plasmid is shown in SEQ ID NO: 5, and the translated amino acid sequence is shown in SEQ ID NO: 6.

Finally, mutation sites were introduced into the plasmid pWSK29-lysC through PCR by using primers D340R-F/D340R-R (see Table 1). The resulting plasmids were recovered from the PCR products by removing enzymes in the PCR system and salt ions in the buffer and then being digested with DpnI for 1 h to remove methylated template plasmid DNAs. The plasmids thus treated were transferred into competent cells Tran10. The obtained plasmid with the correct mutations was named as pSLL3. The nucleotide sequence of the lysC mutant carried by this plasmid is shown in SEQ ID NO: 7, and the translated amino acid sequence is shown in SEQ ID NO: 8.

TABLE 1

List of primers used for point mutation

| | | |
|---|---|---|
| SEQ ID NO: 14 | D340P-F | CCTCGCGCGGCATAATATTTCGGTA CCGTTAATCACCACG |
| SEQ ID NO: 15 | D340P-R | CGTGGTGATTAACGGTACCGAAATA TTATGCCGCGCGAGG |
| SEQ ID NO: 16 | D340V-F | CGCGGCATAATATTTCGGTAGTCTT AATCACCACG |
| SEQ ID NO: 17 | D340V-R | CGTGGTGATTAAGACTACCGAAATA TTATGCCGCG |
| SEQ ID NO: 18 | D340R-F | CGCGCGGCATAATATTTCGGTACGC TTAATCACCACG |
| SEQ ID NO: 19 | D340R-R | CGTGGTGATTAAGCGTACCGAAATA TTATGCCGCGCG |

EXAMPLE 2

Measuring In Vitro Effects of the AK III Mutants

1. Expression of AK III

The above constructed wild-type plasmid pWSK29-lysC and mutant plasmids pSLL1, pSLL2 and pSLL3 were electrically transformed into E. coli GT3 strain respectively (see Theze, J., Margarita, D., Cohen, G N, Borne, F., and Patte, J C, Mapping of the structural genes of the three aspartokinases and of the two homoserine dehydrogenases of Escherichia coli K-12 J. Bacteriol, 117, 133-143 (1974); also see US005661012A), and the obtained strains were named respectively as E.coliGT3 (pWSK29-lysC), E.coliGT3 (pSLL1), E.coliGT3 (pSLL2) and E.coliGT3 (pSLL3), for achieving constitutive expression thereof.

2. Evaluation of the Enzyme Activity of AK III

E.coliGT3 (pWSK29-lysC), E.coliGT3 (pSLL1), E.coliGT3 (pSLL2) and E.coliGT3 (pSLL3) strains were cultured, respectively, in LB medium at 37° C. overnight, and then each inoculated at a ratio of 2% into 50 ml LB medium in 500 ml flasks supplemented with 50 mg/L of ampicillin, and cultured at 37° C., 200 rpm to OD600 of about 0.6. Cultured cells were collected, washed with 20 mM of Tris-HCl (pH 7.5) buffer for 1 time, resuspended in 3 ml of buffer containing 20 mM of Tris-HCl (pH 7.5), sonicated at 200 W for 10 mins (paused for 3 seconds per 1 second sonication), and then centrifuged at 13000 rpm for 30 mins. The supernatant was taken for used as a crude enzyme solution.

Determination of enzyme activity: 1 ml reaction liquid contained 200 mM Tris-HCl (pH 7.5), 10 mM MgSO$_4$.6H$_2$O, 10 mM L-aspartic acid, 10 mM ATP, 160 mM hydroxylamine hydrochloride, an appropriate amount of the crude enzyme solution and L-lysine at desired concentrations. Reaction was performed at 37° C. for 20 mins. 1 ml of 5% (w/v) FeCl$_3$ was added to terminate enzyme activity. 200 ul was taken to measure OD540 on a microplate reader (Black and Wright, 1954).

The results are shown in FIG. 1, in the presence of 1 mM lysine, the wild type AK III retained only about 80% of the activity; and in the presence of 10 mM lysine, retained about 40% of the activity, indicating that enzyme activity was inhibited by lysine feedback; while in the presence of 100 mM lysine, residual enzyme activity for the three mutants was 100%, indicating that amino acid mutations at position 340 can effectively eliminate lysine feedback inhibition.

EXAMPLE 3

Ability of Wild-type and Mutant AK III to Produce L-Lys

Each of the above constructed wild-type plasmid pWSK29-lysC and mutant plasmids pSLL1, pSLL2 and pSLL3 was electrically transformed into the SCEcL3 strain (an *E. coli* mutant strain constructed in laboratory, *E. Coli* MG1655ΔadhEΔackAΔptaΔldhAΔfocAΔpflBΔpoxBΔthr ABΔlcdC) (see Kaemwich Jantama, Xueli Zhang, J C Moore, K T Shanmugam, S A Svoronos, L O Ingram Eliminating side products and increasing succinate yields in engineered strains of *Escherichia coli* C. Biotechnology and Bioengineering, Vol. 101, No. 5, Dec. 1, 2008, *E.coli*MG1655 was used as original strain, and the encoding sequences for 10 genes, adhE, ackA, pta, ldhA, focA, pflB, poxB, thrA, thrB and lcdC were sequentially knockout by red recombination, thereby obtaining mutants), and the obtained strains were named as SCEcL3 (pWSK29-lysC), SCEcL3 (pSLL1), SCEcL3 (pSLL2) and SCEcL3 (pSLL3), for producing lysine through fermentation.

The fermentation medium was as follows: Glucose 40 g/L, ammonium sulfate 10 g/L, phosphoric acid 0.6 mL/L, KCl 0.8 g/L, betaine 0.4 g/L, magnesium sulfate 1.2 g/L, manganese sulfate 0.03 g/L, ferrous sulfate 0.03 g/L, corn steep liquor organic nitrogen 0.4 g/L, 5% antifoaming agent 0.5 mL/L, threonine 0.2 g/L. High-throughput shaker with controlled pH (Huihetang Bioengineering equipment (shanghai) CO. Ltd.) was used for fermentation. Into a 500 ml flask, 100 mL of fermentation medium supplemented with 50 ug/mL ampicillin was added, 2 mL LB broth cultured overnight was inoculated and fermented at 37° C., 200 rpm for 20 hrs, pH 6.8 controlled by diluted ammonia.

Lysine productions from SCEcL3 strains in which wild-type AK III and mutants were overexpressed were shown in Table 2. The growth and sugar consumption were almost identical among strains overexpressing wild-type AK III and mutants. However, at 20 hrs when the sugar was almost exhausted, the strain overexpressing mutant AK III produced 0.28-0.54 g/L of lysine, while the strain overexpressing wild type AK III hardly produced any lysine, indicating that lysine production in the mutant was significantly improved as compared with that in the wild type.

TABLE 2

Lysine production in strains overexpressing wild type and mutant AK III

| Strain | Lysine production (g/L) |
| --- | --- |
| SCEcL3(pWSK29-lysC) | 0.06 |
| SCEcL3(pSLL1) | 0.54 |
| SCEcL3(pSLL2) | 0.37 |
| SCEcL3(pSLL3) | 0.28 |

EXAMPLE 4

Specific Enzyme Activity of Wild-type and Mutant AK III in the Absence of Lysine According to the experimental method in Example 2, total protein in crude enzyme solution was quantified by using BCA Protein Quantification Kit (purchased from Bio-Rad, Cat: 23227), and results of specific enzyme activity of wild-type and mutant AK III in the absence of lysine are shown in Table 3.

TABLE 3

Specific enzyme activity of wild-type and mutant AK III in the absence of lysine

| No. | Specific enzyme activity in the absence of lysine (U/mg) |
| --- | --- |
| Wild-type | 258 |
| 340P | 264 |
| 340V | 145 |
| 340R | 122 |

The results showed that: the absolute enzyme activity of the resulting mutant AK III (340P) with aspartic acid at position 340 mutated to proline was not decreased, but slightly increased; whereas, the absolute enzyme activity of the resulting mutant AK III (340V) with aspartic acid at position 340 mutated to valine or the resulting mutant AK III (340R) with aspartic acid at position 340 mutated to arginine slightly decreased as compared with that of the wild type AK III. Nevertheless, combining the results from Examples 2 and 3, the inventors have unexpectedly found that, 340V, 340R and 340P have excellent ability to eliminate lysine feedback inhibition. In the presence of the product (lysine), the relative enzyme activity of 340V or 340R was similar to that of 340P.

EXAMPLE 5

Polypeptides of the Invention with 6-His Tag

Figure 2:
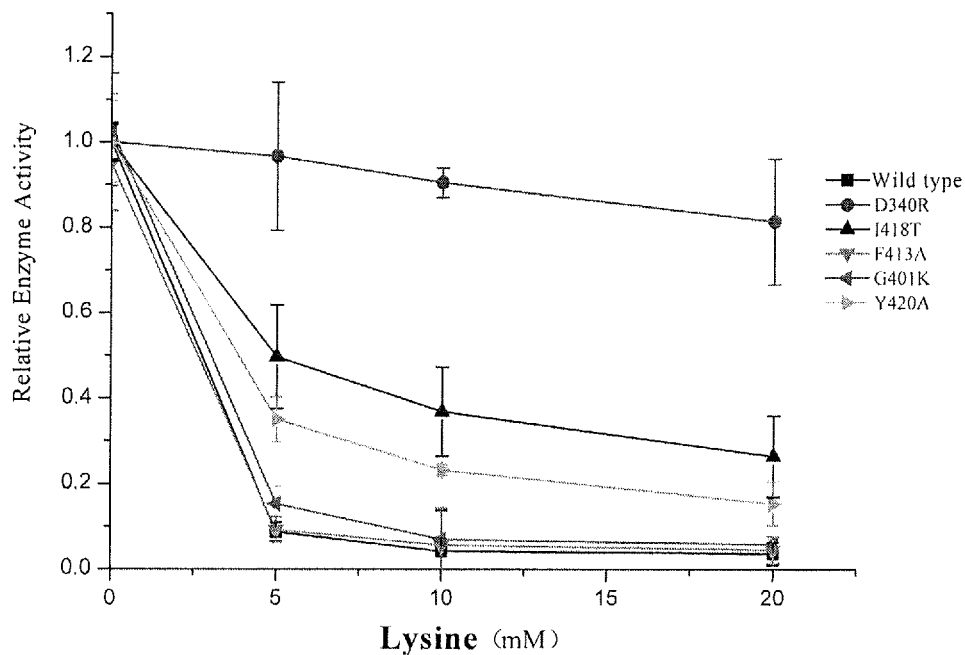
FIG. 2 shows the relative enzyme activity of pure enzymes of the aspartokinase containing 6-His Tag according to the present invention (D340R), and mutants I418T, F413A, G401K and Y420A, as well as the wild type AK III.

The wild type lysC gene, lysC gene with D340R point mutation and lysC gene with I418T point mutation were cloned into plasmid pET21a+ (available from NOVAGEN Corporation) through NdeI and XhoI restriction enzyme sites. The resulting plasmids were electrically transformed into *E. coli* BL21 (DE3), thus achieving LysC protein expression with 6-His tag at the C-terminal. The protein was purified using His SpinTrap columns (purchased from GE Corporation, Cat No. 28-4013-53) according to the method in manufacturer's specification. The enzyme activity of the purified protein was measured by using the method shown in Example 2, and the results are shown in FIG. 2. In this example, the enzyme activity was measured by using a purified enzyme; therefore, there was some difference from the previous examples in which the crude enzyme solution was measured. However, the reflected effects are the same.

The experimental results of this example demonstrated that the further mutated polypeptide obtained by adding a few amino acid residues at either end of the polypeptide of the invention can still have the same or similar function and activity as the polypeptide of the invention.

EXAMPLE 6

Elimination of Feedback Inhibition for AK III with Double Mutations

Wild type AK III was further mutated at 413, 401, 418 and 420 positions by the inventors by using the method of the above examples and the following primers (Table 4). The relative enzyme activity of the resulting mutants were detected, and it was found that the lysine feedback inhibition was not eliminated for the mutants with mutations at 413 and 410 positions in wild type AK III, and the abilities of the mutants with mutations at 418 and 420 positions in wild type AK III to eliminate lysine feedback inhibition were lower than that of the mutant with mutation at position 340 in wild type AK III (FIG. 2).

TABLE 4

List of primers used for point mutations

| | | | |
|---|---|---|---|
| SEQ ID NO: 20 | Y420A-F | CGCATGATTTGT<u>GCT</u>GGCGCATCCAGCCATAACC | |
| SEQ ID NO: 21 | Y420A-R | GGTTATGGCTGGATGCGCC<u>AGC</u>ACAAATCATGCG | |
| SEQ ID NO: 22 | I418T-F | CATTCGCATG<u>AC</u>TTGTTATGGCGCATCCAGCC | |
| SEQ ID NO: 23 | I418T-R | GGCTGGATGCGCCATAACA<u>AGT</u>CATGCGAATG | |
| SEQ ID NO: 24 | F413A-F | GTATTCGGCGTACTGGAACCG<u>GCC</u>ACATTCGC | |
| SEQ ID NO: 25 | F413A-R | GCGAATGTT<u>GGC</u>CGGTTCCAGTACGCCGAATAC | |
| SEQ ID NO: 26 | G401K-F | CCTGTCAAAAGCCTGC<u>AAG</u>GTTGGCAAAGAGGTATTCGGC | |

TABLE 4-continued

List of primers used for point mutations

| | | | |
|---|---|---|---|
| SEQ ID NO: 27 | G401K-R | GCCGAATACCTCTTTGCCAAC<u>CTT</u>GCAGGCTTTTGACAGG | |

In addition to the mutation at position 340, the inventors further mutated AK III at positions 413 and 401, tested the relative enzyme activities of the resulting mutants, and found that AK III mutants with double mutations, such as F413A and G401K, exhibited similar anti-lysine feedback inhibition as the aspartokinase of the invention.

Summing up, the experimental results of this example demonstrated that position 340 is essential for the ability of aspartokinase to eliminate lysine feedback inhibition, and furthermore, the further mutated polypeptides on the basis of the aspartokinases of the present invention can also have the same or similar function and activity as the aspartokinase of the present invention.

All literatures mentioned in the present application are incorporated by reference herein, as though individually incorporated by reference. Additionally, it should be understood that after reading the above teaching, many variations and modifications may be made by the skilled in the art, and these equivalents also fall within the scope of the present invention as defined by the appended claims.

The invention claimed is:

1. An aspartokinase, wherein an amino acid sequence of said aspartokinase has 80% or higher sequence identity with SEQ ID NO: 2 and has an amino acid residue that is not aspartic acid at a position corresponding to position 340 in the amino acid sequence of SEQ ID NO: 2, and
wherein said aspartokinase has a kinase activity on aspartate, and a lysine feedback inhibition of said aspartokinase is relieved.

2. The aspartokinase according to claim 1, wherein the position corresponding to the position 340 in the amino acid sequence of SEQ ID NO: 2 is at least one amino acid selected from the following amino acids: Pro, Ala, Arg, Lys, Gln, Asn, Val, Ile, Leu, Met, and Phe.

3. The aspartokinase according to claim 2,
wherein the aspartokinase:
a) has the amino acid sequence of SEQ ID NO: 4, 6 or 8; or
b) is derived from a), wherein the aspartokinase comprises an amino acid sequence modified through substitution, deletion or addition of amino acid residues from the sequence defined in a), the aspartokinase has a kinase activity on aspartate, and the amino acid sequence of the aspartokinase has at least one amino acid selected from the group consisting of Pro, Arg, and Val at the position corresponding to the position 340 in the amino acid sequence of SEQ ID NO: 2.

4. The aspartokinase according to claim 3, wherein the amino acid sequence of said aspartokinase is SEQ ID NO: 4, 6 or 8.

5. A method for production of L-amino acid, wherein said method comprises culturing a host cell expressing the aspartokinase according to claim 1 to produce L-amino acid.

6. The method according to claim 5, wherein said L-amino acid is L-lysine, L-threonine, L-methionine, L-isoleucine, or L-valine.

7. A method for production of L-lysine, L-threonine, L-methionine, L-isoleucine or L-valine, wherein said method comprises the following steps:
a) providing the aspartokinase according to claim 1 to catalyze a reaction shown below to obtain L-lysine, L-threonine, L-methionine, L-isoleucine, or L-valine,

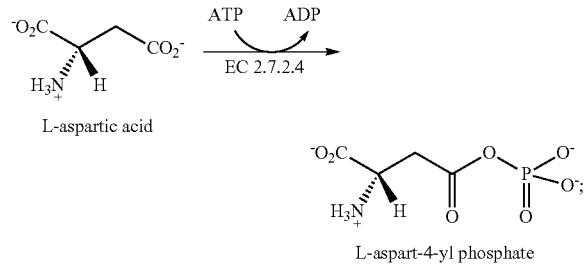

and
b) isolating the L-lysine, L-threonine, L-methionine, L-isoleucine, or L-valine from the above reaction.

8. A method for production of the aspartokinase according to claim 1, wherein said method comprises the following steps:
a) obtaining an encoding sequence of the aspartokinase according to claim 1;
b) transferring the encoding sequence obtained in a) into a suitable host cell by direct chromosomal integration or via a vector;
c) culturing the suitable host cells obtained in b);
d) isolating the aspartokinase of claim 1 produced by said suitable host cells from a culture culturing system obtained in step c); and
e) determining ability of said aspartokinase isolated in step d) to release a lysine feedback inhibition.

9. A method for modifying a wild-type aspartokinase to release a feedback inhibition of L-lysine, said method comprising the following steps:
a) aligning an amino acid sequence of the wild-type aspartokinase with the amino acid sequence of SEQ ID NO: 2; and
b) modifying an encoding sequence for the wild-type aspartokinase such that the encoded amino acid sequence has an amino acid residue at the position corresponding to position 340 in the amino acid sequence of SEQ ID NO: 2 that is mutated to an amino acid other than aspartic acid;
c) transferring the encoding sequence obtained in b) into a suitable host cell by direct chromosomal integration or via a vector;
d) culturing the host cells obtained in c);
e) isolating the aspartokinase of claim 1 produced by said suitable host cells from the culture culturing system obtained in step d); and
f) determining ability of said aspartokinase isolated in step e) to release a lysine feedback inhibition.

10. The aspartokinase according to claim 2, wherein the amino acid sequence of said aspartokinase has at least one amino acid selected from the group consisting of Pro, Arg, and Val at the position corresponding to the position 340 of the amino acid sequence of SEQ ID NO: 2.

11. A host cell comprising the aspartokinase according to claim 1.

12. The host cell according to claim 11, wherein said host cell is from the genus *Escherichia, Corynebacterium, Brevibacterium sp., Bacillus, Serratia* or *Vibrio*.

13. The host cell according to claim 11, wherein an activity of one or more enzymes encoded by a gene selected from the following group is attenuated:
a) adhE gene encoding alcohol dehydrogenase;
b) ackA gene encoding acetate kinase;
c) pta gene encoding phosphate acetyltransferase;
d) ldhA gene encoding lactate dehydrogenase;
e) focA gene encoding formate transporter;
f) pAB gene encoding pyruvate formate lyase;
g) poxB gene encoding pyruvate oxidase;
h) thrA gene encoding aspartokinase I and homoserine dehydrogenase I bifunctional enzyme;
i) thrB gene encoding homoserine kinase;
j) ldcC gene encoding lysine decarboxylase; and
k) cadA gene encoding lysine decarboxylase.

14. The host cell according to claim 11, wherein an activity of one or more enzymes encoded by a gene selected from the following group is enhanced:
a) dapA gene encoding dihydrodipicolinate synthase for eliminating lysine feedback inhibition;
b) dapB gene encoding dihydrodipicolinate reductase;
c) ddh gene encoding diaminopimelate dehydrogenase;
d) dapD encoding tetrahydrodipicolinate succinylase and dapE encoding succinyl diaminopimelate deacylase;
e) asd gene encoding aspartate - semialdehyde dehydrogenase;
f) PPC gene encoding phosphoenolpyruvate carboxylase; and g) pntAB gene encoding nicotinamide adenine dinucleotide transhydrogenase.

\* \* \* \* \*